(12) United States Patent
Ashman

(10) Patent No.: US 6,492,573 B1
(45) Date of Patent: Dec. 10, 2002

(54) BIOCOMPATIBLE ORAL BANDAGE, APPLICATION AND METHOD OF MANUFACTURE

(76) Inventor: Arthur Ashman, 153 Bayberry La., Westport, CT (US) 06880

(*) Notice: Subject to any disclaimer, the term of this patent is extended or adjusted under 35 U.S.C. 154(b) by 0 days.

(21) Appl. No.: 09/641,077

(22) Filed: Aug. 17, 2000

(51) Int. Cl.$^7$ .............................. A61F 13/00; A61C 5/14
(52) U.S. Cl. .............................. 602/54; 602/42; 602/52; 433/136
(58) Field of Search .................................. 206/440, 441; 128/859, 888, 889; 433/206, 207, 215, 218, 219, 223, 9; 602/41–59; 604/307

(56) References Cited

U.S. PATENT DOCUMENTS

| | | | |
|---|---|---|---|
| 5,059,189 A | * | 10/1991 | Cilento et al. .............. 604/307 |
| 5,438,988 A | | 8/1995 | Duan et al. |
| 5,499,966 A | | 3/1996 | Bulley et al. |
| 6,075,177 A | | 6/2000 | Bahia et al. |
| 6,143,805 A | | 11/2000 | Hickey et al. |
| 6,333,093 B1 | * | 12/2001 | Burrell et al. .............. 428/194 |

* cited by examiner

Primary Examiner—Kim M. Lewis
(74) Attorney, Agent, or Firm—Darby & Darby

(57) ABSTRACT

Biocompatible adhesive protective dressings, and methods of manufacturing and using the same, having properties suitable for use on moist tissues such as gingiva. The dressing may include a flexible sheet, e.g. a metal foil, with an irradiated gamma radiation sensitive adhesive on one surface. The properties of gamma sensitive adhesives are modified by exposure to gamma radiation so as to increase their adhesiveness and volume. The dressing may be applied to human or animal tissue to protect the tissue from the environment, and retain autogenous and other substances at the application site. The dressing may be used at surgical sites or wounds.

18 Claims, 4 Drawing Sheets

BIOCOMPATIBLE ORAL BANDAGE, APPLICATION AND METHOD OF MANUFACTURE

BACKGROUND OF THE INVENTION

1. Field of the Invention

The invention pertains to protective dressings, and more particularly to adhesive protective dressings that may be used with animal or human tissue to promote healing, particularly of an oral cavity wound or surgical site.

2. Description of Related Art

It is generally desirable to protect wounded human or animal tissues, particularly oral tissue after gingival surgery, e.g., after tooth extraction. A recent surgical site or wound, in addition to being uncomfortable or painful, is susceptible to infection. Further, lingual and masticatory action, saliva and fluid flow, and food and debris entering an oral wound can delay clotting or dislodge a clot and interfere with healing.

Typically, after oral surgery the surgical incision is often sutured and a cotton dressing (gauze) or a periodontal pack is placed on the surgical site. The dressing's primary purposes are to apply pressure to the wound to help stop bleeding, provide some protection against contaminants, and act as temporary physical barrier to the oral environment. However, a dressing that is made of an absorbent material, such as cotton or the like, has limited ability to prevent moisture and saliva from reaching the surgical site and itself may become saturated, rendering it useless. Moreover, the dressing is held in place by either compression by the patient, e.g., biting down, or by wedging the pack between adjacent teeth. These methods do not reliably hold the dressing in place and it may be dislodged by lingual and masticatory action, and in any event, does not provide an adequate seal to prevent particles and/or moisture, e.g., saliva, from reaching the site. Such a dressing is only effectively used for perhaps a few hours after surgery.

It would be desirable to use a dressing that would prevent moisture from reaching a surgical site or wound, adequately seal the site from the environment, be pliable and imporous, and be sufficiently adhesive to the site to be reliably retained to it for sufficient time to allow healing to begin without interference from the oral environment. In cases where the wound or surgical site has been sutured, the patient also may need to return to the surgeon's office at a later date to have them removed.

Numerous materials are known that are both moisture proof, imporous and biocompatible, so as not to not cause physical or chemical damage to the tissues. Such materials include, for example, metals, plastics, vinyls, and hydrogels. These materials are also available in pliable form, e.g., metal foil, such as tin or aluminum. Biocompatible adhesives are also known and include waxes, powders, gums, polymers (such as acrylics) and other materials.

U.S. Pat. No. 1,550,425 to Burlew, which is hereby incorporated by reference in its entirety, describes an adhesive covering for protecting dental fillings in teeth from moisture. The covering consists of a thin metal foil upon which is deposited a film or layer of paraffin that is united to the foil by heat so as to resist separation. On the outer surface of the paraffin there is rolled or pressed a coating of finely ground gum tragacanth. Jelenko Company of Armonk, N.Y. sells such a covering as Burlew™ Dryfoil™ and Burlew™ Orthofoil™. In particular, the Jelenko product is 99.8% tin foil. The Dryfoil™ has a thickness of about 0.00075 inches, while the Orthofoil™ has a thickness of about 0.0013 inches. The slightly adhesive wax/powder surface allows the foil to adhere to dried teeth.

However, the Burlew covering possesses insufficient adhesiveness to adhere to gingival tissue, which is moist, and its limited thickness provides only minimal physical protection. In addition, it is not sterile, and thus not suitable for post-surgery wound protection.

Thus, it would be desirable for such a covering to have increased capability to seal protected tissues from the oral environment and increased adhesiveness for retention. It would also be desirable to provide the tissue with increased physical protection of the tissue. It would further be desirable that such a covering would be sterile. In addition, it would be desirable to reduce or eliminate the need for suturing a wound or surgical site.

SUMMARY OF THE INVENTION

The present invention is directed to providing an adhesive dressing, particularly a gingival protectant having the aforementioned desirable properties.

The invention is a biocompatible adhesive protectant covering or bandage for use with human or animal tissues, and methods of producing the same. The invention comprises a flexible, pliable, ductile, imporous, moisture-proof, i.e., impervious to moisture, dressing with an adhesive for adhering the covering to tissues for temporary retention and protection from moisture. The adhesive is suitable for both hard and soft tissues, including moist gingival tissues in the mouth, as opposed to merely hard tissues. The protective covering is preferably easily applied to the tissues and occupies minimal space, which is beneficial in the mouth, allowing it to be opened and closed with ease while effectively preventing contact of the tongue or lips with the tissue. The dressing may be configured so as to be placed upon a surgical site or wound.

The adhesive may comprise a gamma radiation sensitive adhesive. When the adhesive is gamma irradiated or otherwise exposed to gamma radiation, i.e., above normal background radiation levels, it undergoes physical and chemical changes. These changes include an increase in volume and adhesiveness. The degree of increased volume and adhesiveness, or tackiness, increases with increased irradiation. The amount of irradiation of the adhesive protective covering may be varied depending upon the amount of volume increase and adhesiveness desired. The irradiated adhesive may then be applied to tissue and adhere to it, and when utilized with a protective covering or "oral bandage," adhere the covering to the tissue. The increased volume and tackiness may assist the covering in preventing undesirable environmental elements, e.g., in the mouth, from reaching the tissue, and cushioning and/or protecting the tissue from physical impact and contaminants.

The adhesive may be irradiated to a degree so that it will adhere to the tissue for a sufficient time for the tissue to significantly heal. This includes moist tissues that are subject to mechanical forces. Thus, the adhesive, alone or in combination with a protective covering, protects the tissue to promote healing and to minimize the possibility of blood clot breakdown, infection, or contamination, all of which may result in pain and discomfort.

Gamma radiation may also sterilize the adhesive and protective covering, thereby further decreasing the possibility of infection. When sterilized in sealed packaging, the sterility may be maintained until use, which may be years later.

BRIEF DESCRIPTION OF THE DRAWINGS

The foregoing and other features of the present invention will be more readily apparent from the following detailed description and drawings of an illustrative embodiment of the invention where like reference numbers refer to similar elements throughout the several views and in which.

DESCRIPTION OF THE PREFERRED EMBODIMENTS

Figure 1:
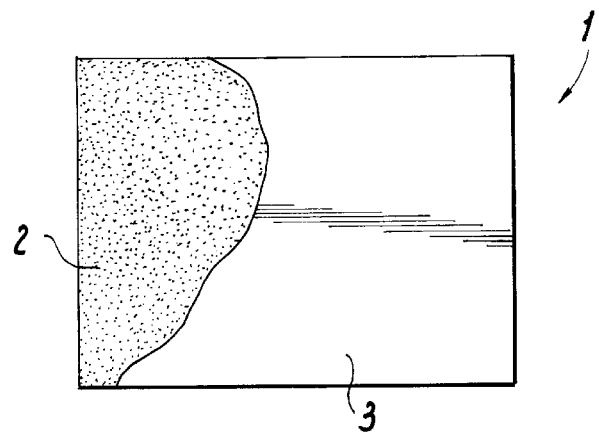
FIG. 1 shows a partially cutaway plan view of an adhesive dressing according to an embodiment of the invention.

As shown in FIG. 1, a wound or surgical protective dressing 1 comprises an adhesive 2 placed on a covering material 3 that may act as a protective covering or bandage, such as, by way of example cloth, vinyl, metal foil, plastic, or hydrogel. The covering material 3 may may be cuttable or reshapeable for any desired configuration, preferably yieldable under finger pressure. Although the dressing 1 is shown as being sheet-like in shape, it may be provided in any desired shape, for example, a strip or as a roll.

Preferably, the covering material 3 is selected to provide desired protective characteristics. For example, if it is desired to limit the amount of moisture reaching the covered tissue, a water-resistant, waterproof or imporous material may be used, such as, for example, a foil, plastic, vinyl or hydrogel.

The adhesive may be any biocompatible adhesive having characteristics suitable for adhering the protective dressing to the tissue. In one embodiment of the invention, the adhesive comprises the wax/powder adhesive of the Jelenko product described above, which may be gamma irradiated to alter its physical and/or chemical characteristics. The adhesive may be gamma irradiated (by any means) sufficient to cause the desired property alteration, such as by a Cobalt-60 source. Those skilled in the art will recognize that if the protective covering is to be irradiated along with the adhesive, e.g., during sterilization, it should be of suitable material to perform its protective function thereafter. In other words, those skilled in the art will be able to select a covering whose functioning is not impaired, i.e., will not deteriorate, upon exposure to the gamma radiation. An examples of water-resistant and imporous coverings that are not adversely affected by gamma radiation are metal foils, such as tin or aluminum.

Figure 2:
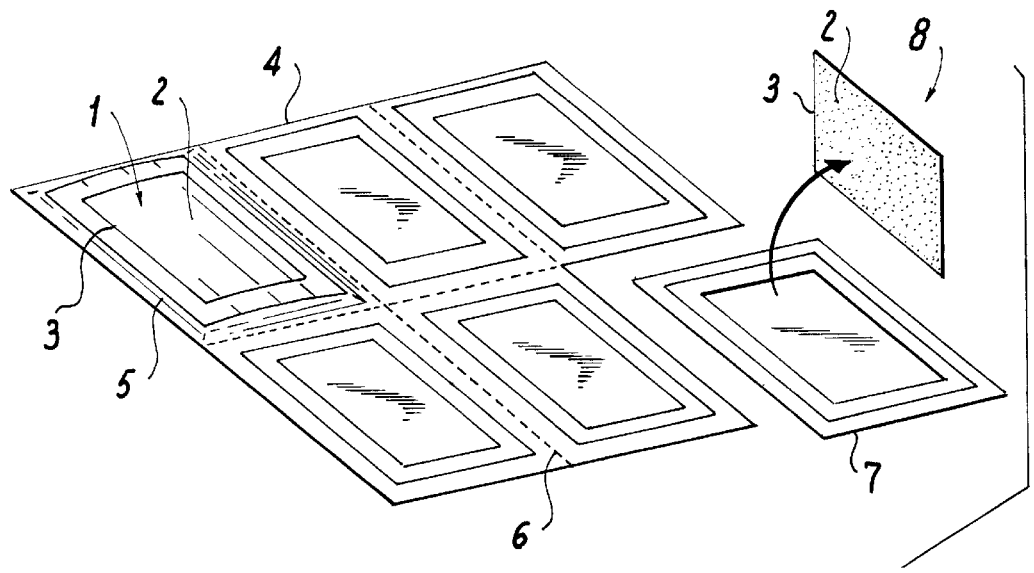
FIG. 2 shows a schematic representation of adhesive dressings in sterile blister packaging according to an embodiment of the invention.

Referring now to FIG. 2, the one or more dressings 1, 8 may be placed in packaging 4, e.g., conventional medical blister packaging, which may be sealed by seals 5, preferably hermetic seals. Although the packaging shown includes six dressings, it will be understood that the packaging can include any number of dressings of any size or combination of sizes. Preferably, each dressing is individually sealed so that one dressing may be removed from the packaging 4 at a time without contaminating other dressings. To this end, the packaging 4 may be provided with perforations 6 or the like to facilitate separation and removal of a single dressing.

The dressings 1, 8, along with the packaging 4, may be gamma irradiated, which preferably, along with its seals 5, is not adversely affected by the radiation. The radiation permanently alters properties of the adhesive, such as adhesiveness and volume. The dressing may be irradiated to the degree necessary to achieve the desired adhesiveness, tackiness and volume increase depending upon the application. Those skilled in the art will recognize that the desired adhesiveness or volume depends upon various factors, including, but not limited to, the tissue upon which the adhesive protectant will be used, the location of the tissue on or in the body, the type of injury or surgery to the tissue, the environment from which the tissue is to be protected, the degree of protection against the environmental factors desired, the type of protective covering to be used, if any, and the length of time for which the adhesive is required to perform its function, e.g., adhere the dressing (bandage) to the tissue. Those in the field will be able to assess the various factors and irradiate the adhesive to obtain the desired characteristics. By way of example, irradiation of the adhesive with at least about 25 kGy of gamma radiation achieves an increase in adhesiveness and volume so as to adequately adhere to and protect surgical tissues from moisture in the mouth, e.g., gum or gingival tissue.

In certain embodiments of the invention, the adhesive, along with any protective covering, is sterilized. Preferably, the adhesive and covering are gamma irradiated with at least about 25 kGy, and more preferably between about 25 kGy and 50 kGy. In FIG. 2, where the protective dressings 1, 8 are sealed in the packaging 4 prior to irradiation, sterilization also sterilizes the packaging, so that sterility of the dressing is maintained until the packaging is opened for use.

Figure 3:
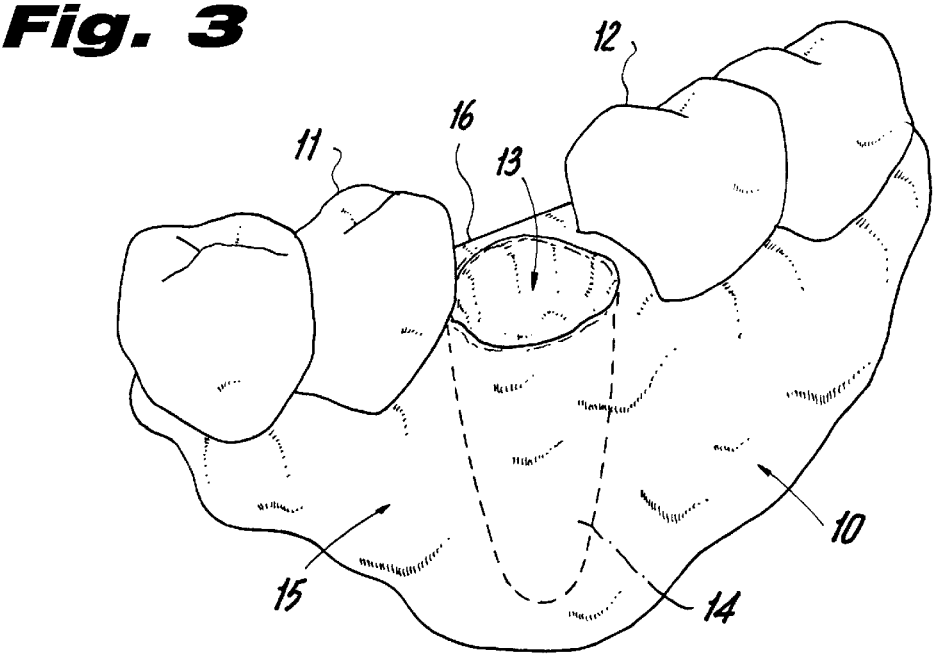
FIG. 3 shows a schematic representation of a portion of a jaw with a tooth extraction socket.

Referring now also to FIG. 3, a jaw 10 containing teeth 11, 12 has had a tooth (not shown) extracted, leaving an extraction site 13 with an extraction socket 14, which may be generally conical in shape, in the jaw bone 15 below the gum tissue 16. Although an extraction site is shown for a tooth having only one root, i.e., a bicuspid, those skilled in the art will understand that the invention may be utilized on any extraction site within the mouth, including teeth having two, three or four roots. After extraction, the jaw bone 15 and incised gum tissue 16 are exposed to the environment in the mouth, which in addition to possibly causing pain to the patient, can lead to infection and debris in the extraction site and thereby delaying or preventing healing.

In order to place a dressing upon the surgical site or wound, a portion 7 of the blister packaging 4 is opened and an irradiated adhesive dressing 8, preferably sterilized (e.g., with between 25 and 55 kGY of gamma irradiation), is removed. In this manner, the other dressings, e.g., 1, in the packaging 4, remain sealed and sterilized.

Referring to FIGS. 4a, 4b, 5a, and 5b, the dressing 8 may be trimmed to a desired size and shape, preferably matching the contours and dimensions of the area to be covered, e.g., the gingival tissue at and adjacent to the wound site. It is also preferable that the dressing not overly interfere with oral function, e.g., speaking. For example, in FIG. 4a, the dressing 8 may be trimmed to have contoured lateral edges 17a, 17b so that the dressing 8 fits between the adjacent teeth 11, 12 and generally follows the contours 18, 19 of the teeth 11, 12 and gingival tissue 16 adjacent to the extraction site 13, i.e., the dressing 8 contacts soft tissue, e.g., gingiva, only.

Figure 4A:
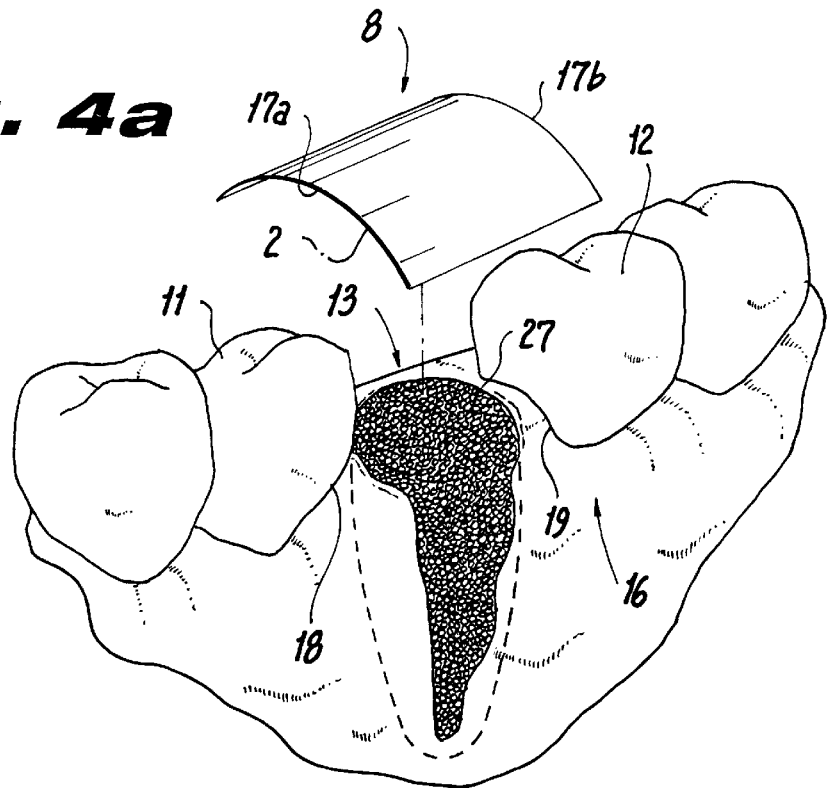
FIGS. 4a and 4b show schematic representations of the jaw of FIG. 3 that has been prepared for application of a dressing according to embodiments of the invention.
Figure 4B:
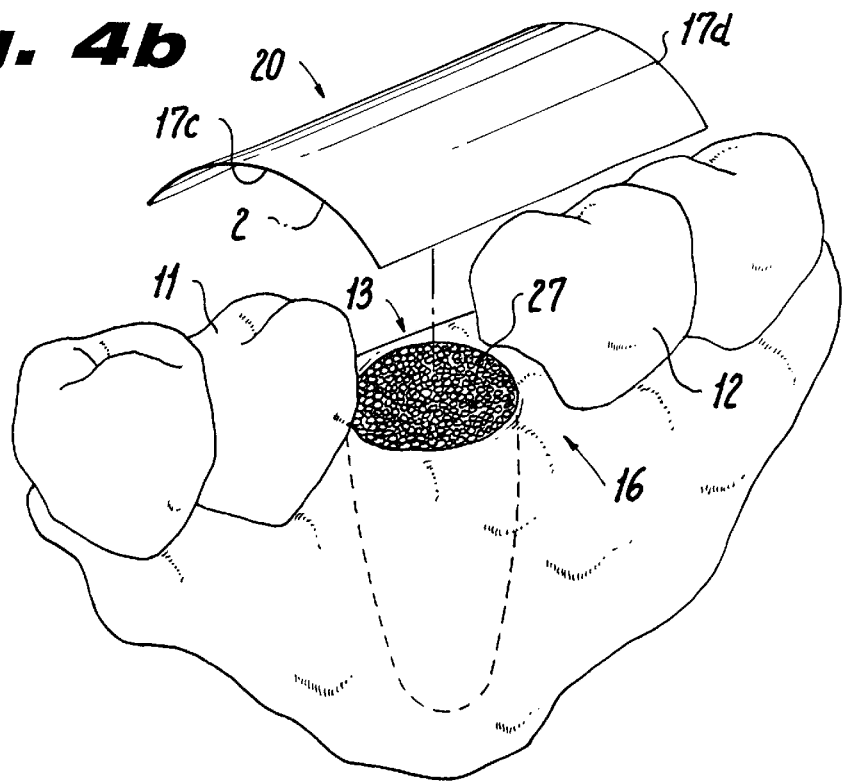

In the embodiment shown in FIG. 4b, protective dressing 20, whose composition may be similar to dressing 8, has a contoured edge 17c so as to generally follow the contour 18 of tooth 11, but the other lateral edge 17d of the dressing 20 has not been contoured or trimmed and may overlap adjacent, e.g., one or two, teeth. Alternatively, the dressing may not be trimmed or multiple dressings may be used.

In order to place the dressing 8, 20 on the extraction site 13, the dressing 8, 20 is positioned over the extraction site 13 with the adhesive 2 facing toward the soft tissue. The dressing 8, 20 is applied against the gum tissue 16, preferably on the buccal and lingual sides. It may also extend over adjacent teeth, e.g., 12, if desired by the surgeon or operating nurse.

Figure 5A:
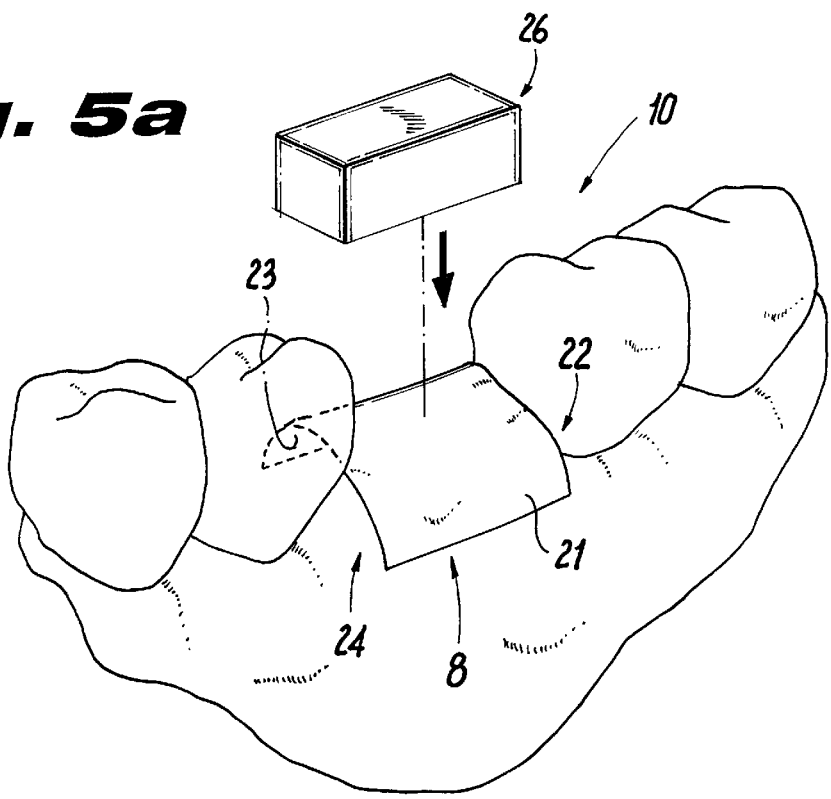
FIGS. 5a and 5b show schematic representations of the jaws of FIGS. 4a and 4b, respectively, with a dressing applied according to embodiments of the invention.
Figure 5B:
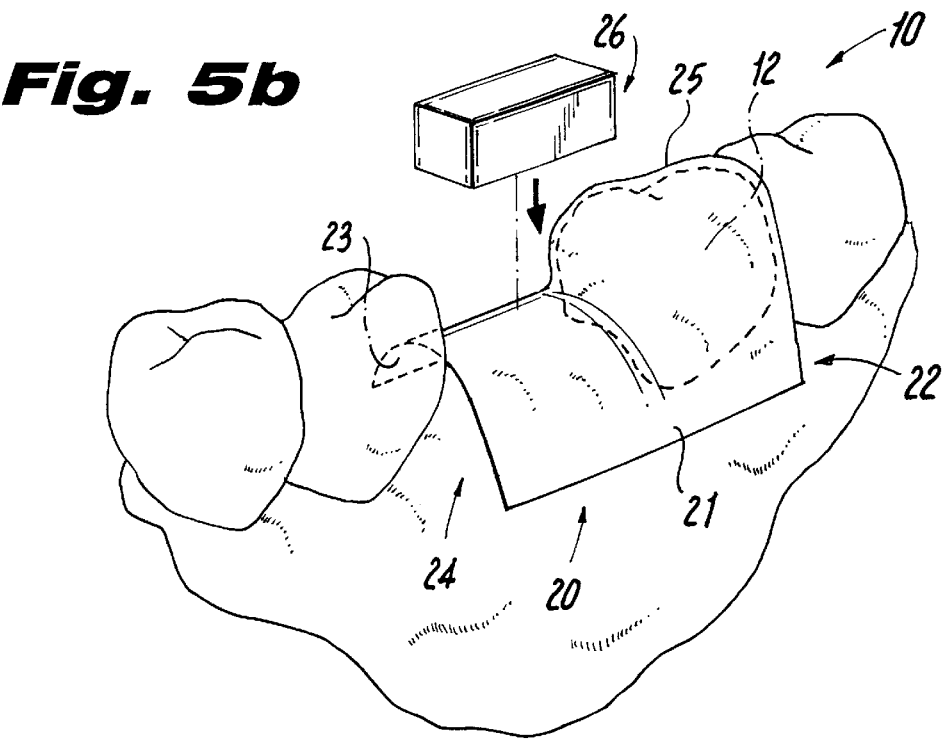

Preferably, the dressing 8, 20 is applied to the jaw 10 to provide optimum protection to the surgical site 13, i.e., to isolate the surgical site from the oral environment. For example, dressing 8 may be configured upon placement so that a portion 21 of the dressing 8, 20 is applied to the buccal side 22 of the jaw 10, and another portion 23 of the dressing is applied to the lingual side 24 of the jaw 10 (FIGS. 5a, 5b). In addition, in embodiments where the dressing overlaps adjacent teeth, as in FIGS. 4b and 5b, the overlapping portion 25 of the dressing 20 is configured to generally conform to the shape of tooth 12. Also preferably, the adhesive 2 may be distributed on the area so that if assists the covering 3 in sealing the site 13 from the oral environment.

Further, in a preferred method of applying the dressing, before the dressing is applied, the gingiva 16 surrounding the extraction site 13 is dried in order to increase initial adhesion of the dressing to the gum 16. This may be accomplished with cotton swabs and/or air, e.g., compressed air. This drying may assist in accurate placement of the dressing on the jaw 10. Also, for certain types of adhesives, for example, waxes and powders, the adhesive 2 is preferably moistened before application, e.g., with water or sterile saline so as to aid initial adhesion and placement.

With the adhesive dressing applied to the surgical site or wound, saliva, food, and oral debris are prevented from reaching the gingival tissue. It is also protected from masticatory and lingual tongue action while healing occurs. The adhesive protective dressing also helps retain blood at the surgical site, which clots and helps to stop bleeding, thus reducing or eliminating the need for suturing the gum tissue. Autogenous bone cells, present in the retained blood from the marrow at the socket periphery, clot and assist in regeneration of bone. The adhesive covering helps prevent this beneficial blood material from being dislodged, broken down, or washed away in the oral environment. This clot protection also occurs when a bone graft material, e.g., Bioplant® HTR®, available from Bioplant, Inc. of South Norwalk, Conn. has been mixed with the bleeding marrow and placed into the extraction socket, as described below.

The dressing 8, 20 may be left on the gum tissue until sufficient healing has occurred, which may be up to seven days or longer, and preferably is about one day to one week. If necessary, adhesive retention of the dressing 8, 20 may be aided by use of a periodontal gum pack 26 (FIGS. 5a & 5b). The periodontal pack 26 may be an absorbent, e.g. cotton, material. It may be placed over the dressing 8, 20 so that the periodontal pack 26 is held in place by the wedging action of adjacent teeth 11, 12, e.g., by wedging the pack 26 between the teeth 11, 12.

Preferably, the adhesive's characteristics allow the dressing to be removed from the surgical site without excessive difficulty and any adhesive remaining on the tissues also may be removed. For example, the adhesive disclosed by Burlew, either in irradiated or non-irradiated state, permits the dressing to be removed from the site without tearing of the dressing or excessive pulling on the tissues, blood clot/graft material, or implant, which can cause pain or damage. Any adhesive remaining on the tissues may be removed mechanically, e.g., gentle scraping, or will be removed by natural oral function, e.g., natural saliva flow, eating, drinking, and/or lingual action (speaking). As will be recognized by those skilled in the art, there afre various known biocompatible adhesives exhibiting such properties, e.g., water-soluble waxes and gums such as gum tragacanth.

Figure 6:
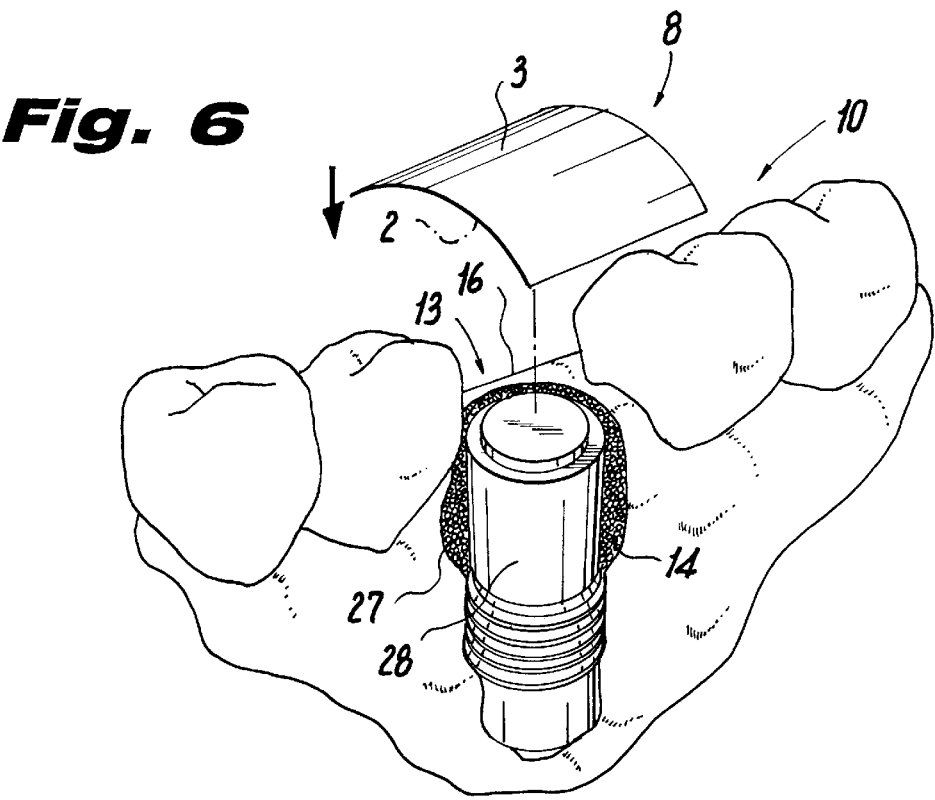
FIG. 6 shows a schematic representations of the jaw of FIG. 3 in which an implant has been installed in an extraction socket according to an embodiment of the invention.

Although the above describes one method of utilizing the invention at a wound or surgical site, those skilled in the art will recognize that many variations on the above technique are contemplated by the invention. For example, as shown in FIG. 6, at the tooth extraction site 13 or other site where bone tissue is affected, bleeding marrow may be collected and mixed with graft material 27, e.g., form a paste. This paste may then be placed onto the bone, e.g., in the extraction socket 14. The graft material or paste 27 is, preferably, at least in part, retained by the dressing 8, 20, which is placed over the tissue as earlier described. The blood/graft mixture or paste promotes clotting, healing, and bone regeneration.

The invention contemplates that any suitable graft material may be utilized with a bone tissue wound or surgical site, as would be known to those in art. Examples of such graft material include, but are not limited to, autogenous (from the surgical site or other hard tissue of the patient), xenograft (e.g., bovine), allograft (human derivatives), and alloplast (e.g., ceramic or plastic) materials. Various alloplast materials are disclosed in U.S. Pat. No. 4,536,158 to Bruins and Ashman; and U.S. Pat. Nos. 4,535,485, 4,547,390 and 4,728,570 to Ashman et al., which cover the Bioplant® HTR® material described above. The aforementioned patents are incorporated herein in their entirety.

Referring again to FIG. 6, in yet other embodiments of the invention, the adhesive protective dressing 8 is placed over the site of a recently installed dental implant 28. Dental implants are well-known in the art and may be installed into the edentulous area of a patient's jaw bone to anchor a prosthesis. It is also known that an implant may be installed immediately after a tooth extraction in order to avoid later invasive procedures, which may require removal of bone that has regrown, and to prevent bone resorption at the extraction site, which commonly occurs after tooth extraction. Although FIG. 6 shows a submergible threaded cylinder-type implant, it will be understood that any type of suitable implant may be used, which may be selected for, among other reasons, the location of the extraction and the profile and condition of the anchoring bone. Generally, extraction sockets tend to be conical in shape, and preferably, cylindrical-type implants, or more preferably, conical or U-shaped implants, such as those disclosed in U.S. Pat. No. 4,521,192 of L. I. Linkow, U.S. Pat. No. 2,609,604 of B. F. Sprague, and U.S. Ser. No. 09/248,079 of Ashman et al. which are incorporated by reference in their entirety, may be utilized in order to more closely fit the dimensions of the extraction site. In addition, the area around the implant 28 in the extraction socket 14 may be backfilled with the bone graft material mixture 27 to promote bone regrowth, as described above, which assists in retaining the implant 28.

Once the implant 28 is installed in the bone, the dressing 8 may be applied to the extraction/implant site 13 in the manner discussed above. The dressing 8 retains the bone graft material mixture 27 and blood at the extraction/implant site 13, and protects it from the oral environment. Due to the retentive/protective properties of the dressing 8, the suturing of the gum or gingival tissue 16 normally required after implant installation in a two-stage or a single-stage implant procedure may be avoided or minimized. By way of example, the protective adhesive bandage may be utilized alone, i.e., without sutures, or in addition to sutures to further protect the surgical area. This may reduce or eliminate the need to have to later reopen the gum 16 to install an abutment or other prosthetic component onto the implant 28, resulting in less surgical trauma to the patient.

Those skilled in the art will recognize that the materials and methods of the present invention will have various other uses in addition to the above described embodiments. They will appreciate that the foregoing specification and accompanying drawings are set forth by way of illustration and not limitation of the invention. It will further be appreciated that various modifications and changes may be made therein without departing from the spirit and scope of the present invention, which is to be limited solely by the scope of the appended claims.

What is claimed is:

1. A protective dressing comprising:
   a covering material; and
   a gamma irradiated, gamma radiation sensitive adhesive located on one side of said covering material, said adhesive having been irradiated with gamma radiation in an amount sufficient to alter its adhesive characteristics.

2. The protective dressing of claim 1, wherein the amount of gamma radiation is at least about 25 kGy.

3. The protective dressing of claim 2, wherein said amount of gamma radiation is between about 25 kGy and about 50 kGy.

4. The protective dressing of claim 1 wherein said protective dressing is sterilized.

5. The protective dressing of claim 1 wherein said covering material is substantially imporous and moisture-proof.

6. The protective dressing of claim 5 wherein said covering material is selected from the group consisting of metal foil, plastic, vinyl, and hydrogel.

7. The protective dressing of claim 6 wherein said metal foil is selected from the group consisting of tin and aluminum.

8. The protective dressing of claim 1, said adhesive being adherable to said gingival tissue when either moist or dry.

9. The protective dressing of claim 6, wherein said covering material has a sheet-like form, said covering material being configurable so as to generally conform to contours of said gingival tissue.

10. The protective dressing of claim 9, wherein said covering material is pliable and ductile.

11. A protective dressing for protecting gingival tissue comprising a covering material and an adhesive on one side of said covering material including a gamma-irradiated gamma radiation sensitive adhesive altered in at least one characteristic other than sterility thereby.

12. The protective dressing of claim 11 wherein said protective dressing is sterilized.

13. The protective dressing of claim 11 configured for application to gingival tissue.

14. The protective dressing of claim 11, wherein the amount of gamma radiation is at least about 25 kGy.

15. The protective dressing of claim 11 wherein said covering material is substantially imporous and moisture-proof.

16. A protective dressing for protecting gingival tissues comprising:
   metal foil; and an adhesive on one side of said metal foil comprising paraffin and gum tragacanth, wherein said adhesive has been irradiated with at least about 25 kGy of gamma radiation and altered in at least one characteristic other than sterility thereby.

17. The protective dressing of claim 16, wherein said protective dressing is sterilized.

18. The protective dressing of claim 16, the adhesive being adherable to said gingival tissue when either moist or dry.

* * * * *